United States Patent [19]
Lauer et al.

[11] Patent Number: 5,597,468
[45] Date of Patent: Jan. 28, 1997

[54] CAPILLARY ELECTROPHORESIS

[75] Inventors: Henk H. Lauer, Belmont; Paul D. Grossman, Redwood City; Dennis E. Mead, Campbell, all of Calif.

[73] Assignee: The Perkin-Elmer Corporation, Foster City, Calif.

[21] Appl. No.: 324,359

[22] Filed: Oct. 17, 1994

Related U.S. Application Data

[60] Continuation of Ser. No. 110,449, Aug. 23, 1993, abandoned, which is a division of Ser. No. 461,568, Jan. 5, 1990, Pat. No. 5,240,576, which is a division of Ser. No. 156,430, Feb. 16, 1988, abandoned.

[51] Int. Cl.$^6$ .................... G01N 27/26; G01N 27/447
[52] U.S. Cl. .................. 204/604; 204/453; 204/601; 204/602
[58] Field of Search ................ 204/299 R, 180.1

[56] References Cited

U.S. PATENT DOCUMENTS

| | | | |
|---|---|---|---|
| 4,898,658 | 2/1990 | Karger et al. | 204/180.1 X |
| 5,240,576 | 8/1993 | Lauer et al. | 204/299 R |

OTHER PUBLICATIONS

Richard N. Zare et al "Bias in Quantitative Capillary Zone Electrophoresis Caused by Electrokinetic Sample Injection" Analytical Chemistry, vol. 60, No. 4 (Feb. 1988) 375–372.
James W. Jorgenson and Krynn DeArman Lukas, "Zone Electrophoresis in Open–Tubular Glass Capillaries" Analytical Chemistry, vol. 52, No. 8 (Jul. 1981) 1298–1302.
James W. Jorgenson and Krynn DeArman Lukacs, "Zone Electrophoresis in Open–Tubular Glass Capillaries" Analytical Chemistry, vol. 53, No. 8 (Jul. 1981) 1298–1302.
Richard N. Zare et al "Bias in Quantitative Capillary Zone Electrophoresis Caused by Electrokinetic Sample Injection" Analytical Chemistry, vol. 60, No. 4 (Feb. 15, 1988) 375–377.

*Primary Examiner*—John Niebling
*Assistant Examiner*—John S. Starsiak, Jr.
*Attorney, Agent, or Firm*—Paul D. Grossman; Joseph H. Smith

[57] ABSTRACT

An apparatus is disclosed for providing capillary electrophoresis, which includes an electronically controlled valve system for automatically introducing a sample into the capillary by means of a vacuum at the end of the capillary tube. This approach of sucking in the sample is extremely accurate and reproducible, and results in a minimum of band broadening. Furthermore, it enables the entire capillary electrophoresis sytem to be easily automated. An automated temperature control system is provided which enables the temperature of the capillary tube (and hence the solvent/solute system) to be controlled during electrophoresis, thereby very directly controlling pH and electrophoretic mobility. In another embodiment, the capillary is prewashed and equilibrated to achieve substantially zero charge on the capillary wall, thereby essentially eliminating electroosmotic flow and substantially improving resolution.

3 Claims, 3 Drawing Sheets

| Run Number | Buffer | pH Level | Elution time Electroosmotic Flow (min) | Pre-Wash | Electroosmotic Mobility $10^{-4}$ cm$^2$/Vs |
|---|---|---|---|---|---|
| #1 | Caps (10 nM) | pH = 11.13<br>pH = 11.13 | t = 1.70<br>t = 1.63 | NaOH<br>HCl | 8.2<br>8.5 |
| #2 | Bicene (10 nM) | pH = 8.45<br>pH = 8.45 | t = 1.64<br>t = 1.93 | NaOH<br>HCl | 8.5<br>7.2 |
| #3 | MES (10 nM) | pH = 6.0<br>pH = 6.0 | t = 2.09<br>t = 6.27 | NaOH<br>HCl | 6.7<br>2.2 |
| #4 | MES (10 nM) | pH = 6.0<br>pH = 6.0 | t = 2.07<br>t = 4.80 | NaOH<br>HCl | 6.7<br>2.9 |
| #5 | Citric Acid (20 nM) | pH = 4.0<br>pH = 4.0 | t = 11.82<br>t = 54.6 | NaOH<br>HCl | 1.2<br>0.25 |
| #6 | Citric Acid (20 nM) | pH = 2.51<br>pH = 2.51 | t = 36.53<br>t = 70.31 | NaOH<br>HCl | 0.38<br>0.2 |

Fig. 2

CAPILLARY ELECTROPHORESIS

This is a continuation of application Ser. No. 08/110,449 filed 23 Aug. 1993 now abandoned, which is a division of application Ser. No. 07/461,568, filed Jan. 5, 1990, now U.S. Pat. No. 5,240,576, which is a division of application Ser. No. 07/156,430 filed Feb. 16, 1988, now abandoned.

BACKGROUND OF THE INVENTION

This invention relates to capillary electrephoresis, or as it is more conventionally called "capillary zone eiectrophoresis" (CZE), and more particularly to automated methods and apparatus for introducing samples into capillary columns and for improving separations by using temperature control of said columns.

In recent years significant advances have been made in micro-column separation techniques. A principal advantage of such techniques is their suitability for analysis of extremely small sample volumes, eq. in the microliter or submicroliter amounts of sample. Being able to analyze such small volumes has become exceedingly important with the explosion of research in the biological field, because oftentimes biological samples are quite small.

One of the significant problems with capillary techniques is in introducing sample into the capillary. One technique used in capillary electrophoresis, called sample injection, is electromigration, a term collectively including the effects of eletrophoresis and electro-osmosis (See Jorgenson, J. W, and Lukacs, K. D., *J. Chromatography*, 1981, Vol. 218, pp. 209–216; Jorgenson, J. W., and Lukacs, K. D., *Science* 1983 Vol 222 pp. 266–272; and Wallingford, R. A. and Ewing, A. G., *Anal. Chem.*, 1987, vol. 59, pp. 681–684). In this technique, one end of the capillary and the electrophoresis anode are placed into the sample and a voltage is briefly applied, causing a small band of sample to electromigrate into the capillary. This method of sample injection suffers from discrimination within the sample because solutes with higher mobilities will preferentially migrate into the electrophoresis column and therefore change the relative composition of the sample. To avoid this problem, attempts to physically inject sample have also been reported (Jorgenson and Lukacs, Science, ibid). However these direct injection techniques cause band broadening, apparently due to the laminar flow profile introduced during the injection.

Other less common injection methods include Gravity flow (See Tsuda, A., et al, *J. Chromatography*, 1983, Vol. 264, pp. 385–392.), siphoning (See Honda, S. et al, *J. Chromatography*, 1987, Vol. 404, pp. 313–320.), and the use of an electonic sample splitter (See Deml, M. et al, *J. Chromatography*, 1985, Vol. 320, pp. 159–165.). Each of these injection techniques are capable of placing subnanoliter volumes of sample into the electrophoresis column with a minimum of band broadening. However, the gravity flow or siphoning injection method is inaccurate and lacks precision in providing absolute volume amounts due to the unreliable position of the sample level which will change due to the sample withdrawal. The latter can only be neglected if the original sample volume is large compared to the volume injected. With the electronic splitter, a larger initial sample volume is required in order be able to split it down to the smaller size required for the column. Thus, some sample may be wasted, or there may not be sufficient sample to perform a separation. Also, this latter technique is further complicated by requiring an additional controlled power supply or very careful control of the electric resistances in the different legs of the splitter. Furthermore, the need to use an initial larger sample size significantly decreases the number of applications for which it can be used.

What is needed is a simple, automatable, sample injection technique that is suitable for microvolumes, is capable of providing accurate sample volumes, and which produces a minimum of band broadening.

SUMMARY OF THE INVENTION

In accordance with preferred embodiments of the invention, an apparatus is disclosed for providing capillary electrophoresis, which includes an electronically controlled valve system for automatically introducing a sample into the capillary by means of a vacuum at the end of the capillary tube. This approach of sucking in the sample is extremely accurate and reproducible, and results in a minimum of band broadening. Furthermore, it enables the entire capillary electrophoresis sytem to be easily automated.

The apparatus includes first and second reservoirs that are electrically isolated from each other for holding electrophoretic media, a sample reservoir located in proximity of the first reservoir for holding a sample to be electrophoresed, and a high voltage power supply connected between the first reservoir and the second reservoir. A first pressure source of a first gas having a first known pressure, typically the ambient air pressure, is used for providing an environment for the first reservoir and the sample reservoir, so that electrophoretic media in the first reservoir and sample in the sample reservoir are under the first pressure. The apparatus includes a pressure reservoir for holding a second gas (also typically air) having a second pressure that is lower than the first pressure. A capillary tube is also included in which to electrophorese the sample. A rack system is provided for holding the first and second reservoirs, the pressure reservoir, the high voltage power supply, the sample reservoir, and for holding one end of the capillary tube in the second reservoir. A gas connecting system connects the second reservoir to the pressure reservoir, the connecting system having a valve for venting the connecting system to the first pressure source and for blocking communication of the second reservoir with the pressure reservoir while venting to the first pressure source. The apparatus also has an insertion element for inserting the other end of the capillary tube into the sample reservoir and into the first reservoir. In the preferred mode, the apparatus includes a computer system for controlling the insertion element and the valve, so that when the other end of the capillary tube is in the sample reservoir, the valve permits communication of the second reservoir with the pressure reservoir for a controlled period of time for sucking the sample into the capillary tube. Additionally, in the preferred mode, the computer system causes the other end of the capillary tube to be transferred to the first reservoir after the sucking of the sample into the capillary tube. After the sample has been introduced into the capillary tube and the tube has been transferred to the first reservoir, the electrophoresis is begun.

An additional important feature of the preferred embodiment is that an automated temperature control system is provided which enables the temperature of the capillary tube (and hence the solvent/solute system) to be controlled during electrophoresis. This is particularly advantageous in that for many buffers, the pH is a strong function of temperature; hence temperature control is very directly pH control. Additionally the pH can have a direct effect on the electrophoretic mobility and hence the separation efficiency.

In another embodiment of the invention, the capillary is prewashed and equilibrated to achieve substantially zero charge on the capillary wall, thereby essentially eliminating electroosmotic flow and substantially improving resolution.

BRIEF DESCRIPTION OF THE DRAWINGS

FIG. 2 is a table that illustrates the effects of capillary prewash on electroosmotic mobility.

DESCRIPTION OF THE PREFERRED EMBODIMENTS

Figure 1B:
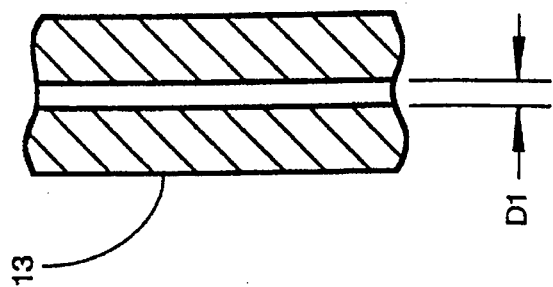
FIG. 1 shows an apparatus according to the invention.
Figure 1A:
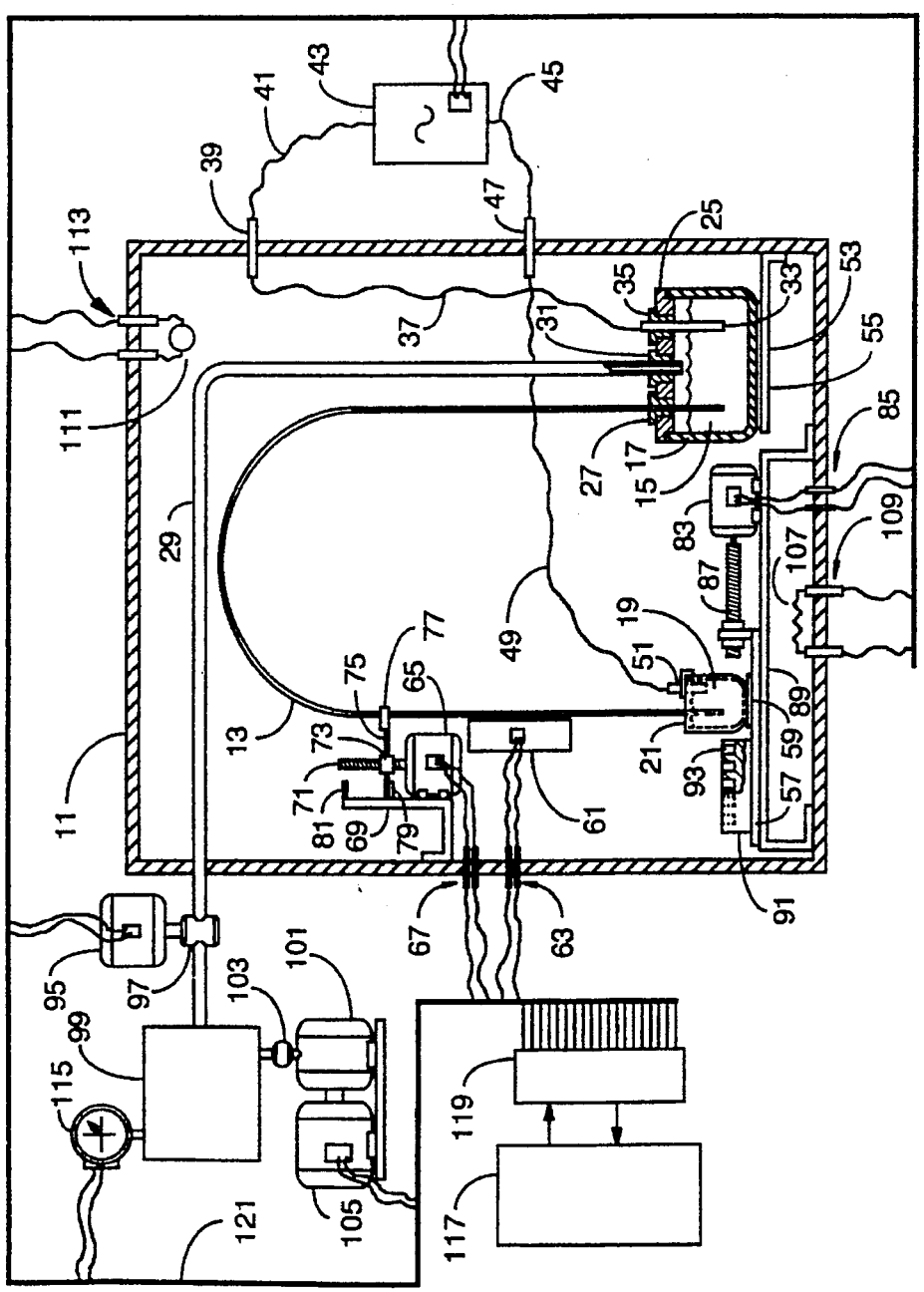

FIG. 1 is a partially sectioned illustration of a preferred embodiment of an automated capillary electrophoresis, henceforth CZE, apparatus according to the invention. In this preferred mode, the apparatus includes an environmental enclosure 11, which has access openings (not shown), and feedthroughs of various kinds through the walls of the enclosure for elements that must be connected to elements outside the enclosure. Electrophoresis is accomplished within the enclosure in a capillary tube 13, preferably constructed of fused silica, such as is typically used for high sensitivity liquid or gas chromatography. One end of capillary 13 is immersed for the process in a buffer solution 19 held in a first container 21, and the other end is immersed in a buffer solution 15 in a second container 17. Buffer solutions 15 and 19 are typically the same solution, and many are well known in the art. Although in the prior art many different pH's have been used for the various buffers, depending on the particular experiment being performed, in this preferred embodiment, it has been found that for capillary electrophoresis that a relatively low pH is best. In the preferred mode, to achieve the best separations, the pH is adjusted to the point of zero electric charge of the buffer-capillary combination, ie. the point at which there is no charge on the capillary wall. As will be discussed subsequently in more detail, the point of zero charge will vary depending on the buffer used and the pretreatment of the column. However, as a practical matter, typically a pH below about 2.5 will suffice. Also, as will be discussed subsequently, sometimes particular buffers are used which are temperature dependent, ie. their pH varies strongly with temperature, or stated another way dpK/dT is relatively large.

View 23 is an enlargement of capillary tube 13 in cross section. The internal diameter of the capillary, D1, varies for different kinds of samples and for other reasons. A typical value for D1 is 0.05 mm, and generally varies between zero and 200 microns. The wall thickness of tube 13 is small enough that the tube is flexible and and may generally be manipulated without breaking. Also, the small diameter allows for efficient heat transfer.

Second container 17 has an airtight top 25. Capillary tube 13 enters the second container through a stopper 27 maintaining an airtight seal. There are two additional penetrations through top 25. A hollow tubing 29 enters through stopper 31 and and an electrode 33 enters through another stopper 35. Stopper 35 is typically of an electrically non-conducting material. From electrode 33, an electrical lead 37 goes to an electrical feedthrough 39 which allows an electrical signal or power to cross the wall of the enclosure without shorting to the enclosure. On the outside, electrical lead 41 goes to a terminal of a high voltage power supply 43.

From the opposite terminal of power supply 43 another electrical lead 45 goes to another feedthrough 47. Inside the enclosure lead 49 goes to an electrode 51 immersed in buffer solution 19 in first container 21. With buffer solution and sample material in the capillary tube and the tube ends immersed in buffer solution in the two containers, power supply 43, through the electrical leads, feedthroughs and electrodes, may be used to maintain an electrical potential across the material in the capillary tube.

The second container rests on a support 53 with an electrical insulator 55 between the container and the support. The insulator is needed if the container and support are electrically conductive. First container 21 rests on a moveable, sliding support 57 and an insulator 59.

A detector 61 is positioned relative to the capillary tube to measure the results of electrophoresis in the capillary. Such detectors are well known in the art, and include for example an Applied Biosystems Model 783 Spectroflow UV/Visible Detector, which is a variable wavelength programmable detector that is specifically adapted for on-column detection. Electrical leads through feedthroughs 63 carry power and signals for the instrument. There may be more than the two leads shown.

When the electrophoresis process is complete on one sample, and another sample is wanted in the capillary for analysis, a new sample may be loaded without manual intervention or disturbing the environmental enclosure. A motor 65 powered by leads through feedthrough 67 and supported by bracket member 69 may be activated to turn lead screw 71. Nut 73 is attached to member 75 with a clamp 77 securely holding tube 13, so that turning lead screw 71 will raise and lower the tube by the distance between stops 79 and 81. This distance is set to be sufficient for the lower end of capillary tube 13 to be raised above the rim of container 21, and lowered again.

With tube 13 raised above the rim of container 21, motor 83 may be activated by leads through feedthroughs 85 to turn lead screw 87 moving slide 57 along support 89. A sample container 91 with multiple microvolumes such as 93, arranged in a row in the container, is prepared in advance and placed adjacent to container 21 on slide 57. Each microvolume may contain a sample to be analyzed. Typical injection volumes range from 1 nl to 10 nl in this preferred mode, although other size samples could of course be chosen depending on the size of the reservoir used to hold the sample and the size of the column. By controlling motor 83 moving slide 57, any one of the microvolumes of container 91 may be moved to be directly below the end of capillary tube 13, which may then be lowered into the microvolume by control of motor 65. Once a new sample is drawn into the capillary, the capillary may again be raised, container 21 returned to position, and the end of the capillary re-immersed in the buffer by lowering the tube.

To inject a new sample, while one end of the capillary is in one of the microvolumes of sample material, a relative vacuum is drawn in second container 17 by means of tubing 29 which exits the environmental enclosure. Motor 95 is controlled to rotate a three-way rotary valve 97 opening tubing 29 to vacuum reservoir 99. The reservoir is maintained at desired vacuum level by vacuum pump 101 through isolation valve 103. A vacuum sensing gauge 115 with programmable signal points monitors the vacuum level in reservoir 99. The pump is powered by motor 105. Careful control of timing and vacuum level provides a very accurate method for drawing a predetermined amount of sample material into the capillary, as well as other benefits. As an example, using a pressure differential of 5.0 in. of Hg between the vacuum reservoir and the enclosure 11, with a 65 cm long fused silica capillary having a 50 micron inside diameter, a 2 second open time for valve 97 results in an injection quantity of 5 nanoliters of an aqueous solution.

Another important feature of the apparatus according to the invention is that the temperature inside the environmental enclosure 11 can be controlled. A heating element 107 is powered through feedthroughs 109 to provide heat, and a heat sensing element 111 monitors temperature through leads 113. As will be discussed subsequently, such provision for temperature control is very useful, since some buffers have a temperature dependent pH, and for those buffers pH can be controlled automatically by controlling temperature. Temperature control is also useful in the more general case since other kinds of variations are avoided if a uniform temperature is used throughout a separation. For example, viscosity and therefore mobility are most often strong functions of temperature, so that for reproducability, temperature control is required.

Power and control leads for all the electrical equipment associated with the apparatus of the preferred embodiment are carried by electrical conduit 121 to a control interface 119 which provides power terminations and switching of signals for control purposes. The control interface is connected to and manipulated by a computer 117 which can be pre-programmed so that critical parameters may be maintained and sequences of analyses may be performed automatically by the apparatus. For example, the vacuum level desired can be entered as control data, and the computer, through the control interface, monitors the signal from vacuum gauge 115 and opens and closes vacuum isolation valve 103 so that the desired vacuum level is closely maintained. As another example, the computer can be used to control the temperature inside the environmental enclosure by monitoring temperature sensor 111 and controlling power to heating element 107 as needed to maintain the programmed temperature. Also, the computer can be programmmed to allow a sequence of analyses to be made, using the several samples preloaded into microvolumes in container 91, controlling the electrical devices in the required sequence. The program may be set to run analyses on all of the microvolume samples, one-after-the other, or to allow for manual intervention and initiation between each analysis. Another important feature of computer control is that the computer makes it possible to reverse polarity of the capillary electronically. Hence, for solutes that are of opposite charge, one can reverse the direction of migration of solute particles and thereby use the UV detector at its fixed location. Details of the program structure for the computer are provided in Appendix A.

Control of pH

In capillary electrophoresis in free solution and in some gels, solutes with different charges (absolute) have different electrophoretic mobilities and can therefore be separated. Separation efficiency can be improved if the selectivity (ie. the relative difference in electrophoretic mobility) between two or more solutes can be changed during the eletrophoretic run. One way to achieve this is to change the relative difference in the effective charges on the species to separated. In many cases the pH (or better, the pK) of the solution in the capillary, which is mostly buffer, determines the charge on solutes that obey the rules of acid/base equilibria. For example, for CHES (Cyclohexyl amino ethane sulfonic acid) in water, a chemical equilibrium is established which is dependent on the particular temperature, as indicated by the following formula:

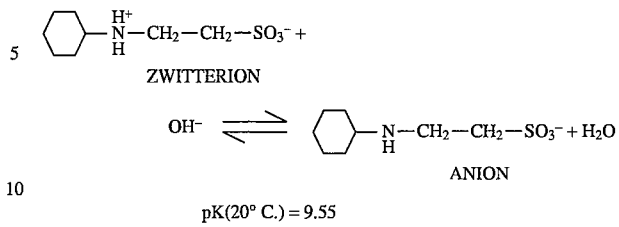

at pH=9.55, 50% of the CHES is in the zwitterion form and 50% is in the anion form. By increasing the pH to 10.55, the anion ($RSO_3^-$) concentration will be ten times that of the zwitterion and by increasing it to 11.55, the equilibrium will be pushed almost completely to the anion side. At that point only 1% of the CHES will exist as a zwitterion. The anion will posess a certain electrophoretic mobility while the zwitterion being electrically neutral will not have an electrophoretic mobility. What this means is that at a pH of about 7.55, the CHES solute will have practically no electrophoretic mobility and at a pH of about 11.55, it will have nearly the mobility of the anion. Hence, by changing the pH of the solution, the mobility of a solute can be changed.

As indicated earlier, in many cases, the pH (or pK) of buffer solutions are a function of their temperature, and different buffer solutions have different temperature characteristics. (See CALBIOCHEM CATALOG, Table IV, Page 16.) By changing the temperature of the buffer in time or in space, different pH's in time and in space can be generated and thus the mobility of a species can be manipulated. In general, the pK of a solution is given by:

$$pK = pH - \log\{RSO_3^-\}/\{R^+SO_3^-\},$$

where $\{RSO_3^-\}$ corresponds to the concentration of the anion $RSO_3^-$, etc., and in many cases the pK has a strong temperature dependence. As an example of how to use this temperature dependence during the performance of a separation, suppose that a separation is to be performed on a solution containing three solutes, A, B, and C, and that the A and B separation is best performed at a first temperature T1 with A coming through first, and that the B and C separation is best performed at a temperature T2. The separation is run for a first time at temperature T1, until A is separated from B and C, then the temperature is changed to T2 until B and C are separated. Similarly, more complicated temperature profiles can be used depending on the particular solutes being separated, for example continuous programming can be used if desired.

It should be appreciated by those skilled in the art that solutes that are to be separated may also obey the acid/base equilibria rules, and as a result also can change their degree of ionization with temperature. This solute effect will be superimposed on the pH change of the solvent (buffer) and hence, depending on the choice of buffer and solute combination, can provide an enhanced mobility difference, decreased mobility difference, or no change in mobility difference at all. Hence, various combinations of buffer and solute should be chosen to achieve the desired effect.

As a specific example of the effects of varying temperature, and hence pH, an experiment was conducted to investigate the relative electrophoretic mobilities of two proteins, Myoglobin (wsm) and Myoglobin (hh). A fused silica capillary was used having a 55 cm length to the detector, a total length of 70 cm, and an inside diameter of 0.050 mm. Using a 10 mM Tris-HCl buffer, and a 20 kV electric potential, the change in relative difference in electrophoretic mobilities (ie. selectivity) of the two proteins was measured between the temperatures of 26.9 C. (pH=8.90) and 62.4 C. (pH= 7.90), and was found to be minus 45%.

As described earlier, another important aspect of the invention in achieving a high selectivity, particularly in protein separations, is to eliminate charge on the capillary wall. The purpose is to eliminate electroosmotic flow, so that the column is not being swept during the run, thereby providing a longer separation time in the column (lower average velocity of the species to be separated), and hence better resolution. Also, by eliminating charge on the wall, positive ions (eg. proteins) do not stick to the wall, unlike the typical case when the wall is negatively charged. One way to achieve zero charge on the wall is through control of pH. Generally, the electroosmotic velocity is proportional to the zeta potential times the applied electric field divided by the viscosity. The zeta potential describes electrostatic forces in the interfacial double layer between two phases and is, among others, a function of the differential adsorption of ions. When there is no electroosmotic flow, the zeta potential is zero, and there is no charge on the capillary wall. Hence, by measuring the electroosmotic mobility, ie. the electroosmotic velocity divided by the applied field, as the pH is changed to achieve zero mobility, the point of zero charge on the wall can be determined.

Figure 3:
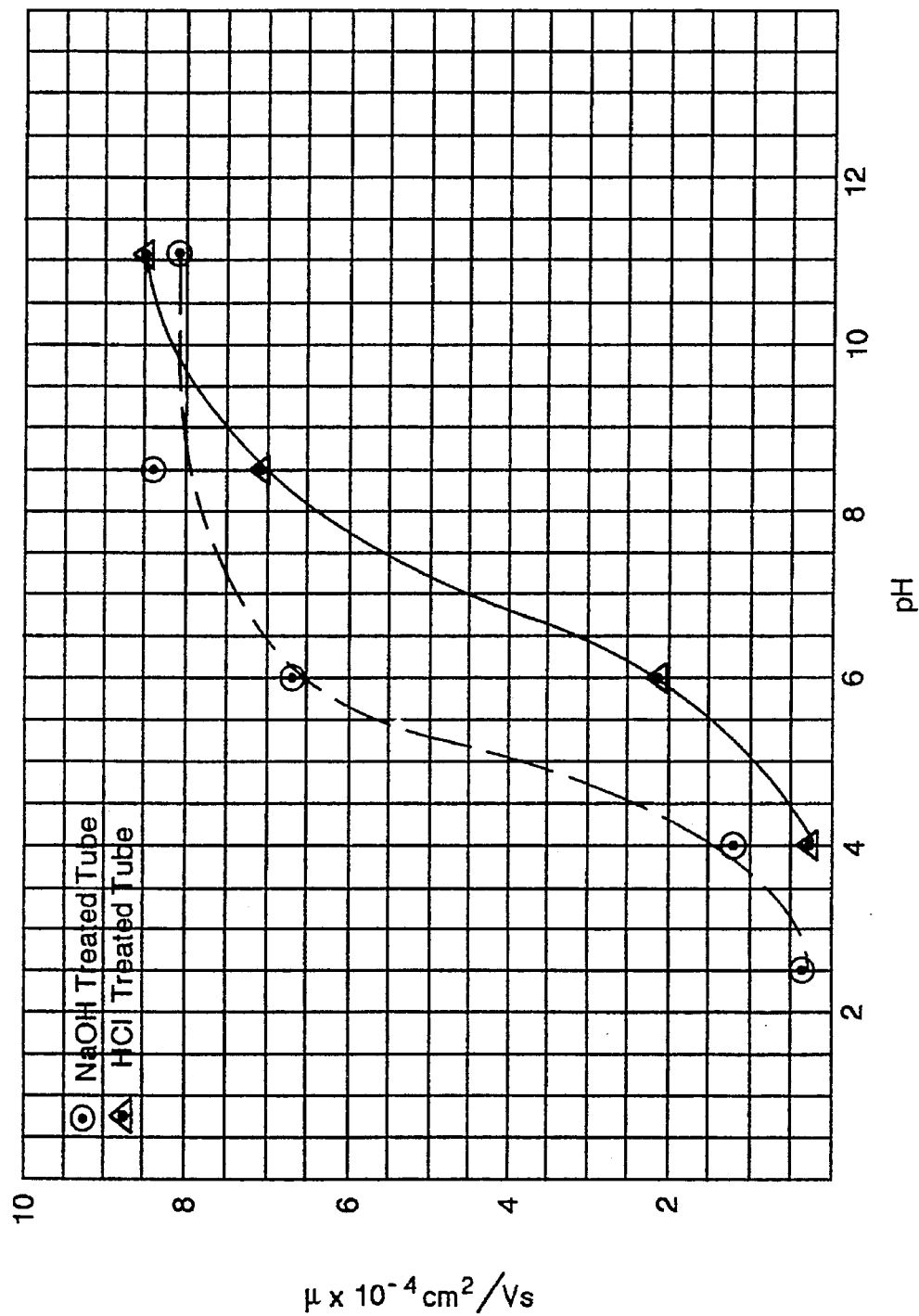
FIG. 3 is a graph showing the results of FIG. 2.

An example of the effects on electroosmotic mobility resulting from pH changes and some surprising results from differences in capillary preparation are illustrated in the Table of FIG. 2, and in FIG. 3. In these experiments, a number of buffers were used in order to cover a wide range of pH levels, since as a general rule any one buffer has a relatively limited range of pH values over which it is useful. The capillary used was a fused silica capillary supplied by Polymicro Technologies, and had a length to the detector of 30 cm, a total length of 50 cm, and an inside diameter of 0.050 mm. The applied electric field used was 360 V/cm. Except for run 4, where the order of preparation was reversed to check for reversibility (ie. steps 4, 5, and 6, preceeded steps 1, 2, and 3 below), the protocol for capillary preparation was as follows:

1. wash capillary with 1M NaOH for 3 minutes;
2. equilibrate with buffer for 5 minutes;
3. run with mesityl oxide as a neutral marker and measure elution time for the marker;
4. wash capillary with 1M HCl for 3 minutes;
5. equilibrate with buffer for 5 minutes;
6. run with mesityl oxide and measure elution time.

The buffers used were CAPS (ie. 3-(cyclohexylamino) propane sulfonic acid), BICINE (ie. N,N-bis (2-hydroxyethyl) glycine), MES (ie. a sodium salt of 2- (N-morpholino) ethane sulfonic acid), and citric acid.

A graph of the electroosmotic mobility, shown in FIG. 3, illustrates dramatically the results of lowering the pH. Clearly, as the pH is lowered there is a sharp decrease in mobility indicating that the charge on the wall is quickly approaching zero. For NaOH treated tubes, a pH of below about 2.5 corresponds essentially to zero electric charge on the wall (the baseline noise is proportional to the current, so as a practical matter it is important to use a low current, and low pH buffer). Even more striking, however, is the effect of the prewash. Although NaOH is the quintessential strong base that is typically used for washing glass, it is clear that the use of a strong acid such a HCl is a much better prewash if the purpose is to eliminate charge on the capillary wall. For example, if the capillary prewash is performed with HCl, a pH of about 4.0 eliminates about 97% of the charge on the capillary wall, and produces an electroosmotic mobility that is even lower than that achieved using a pH of 2.5 if the prewash is with NaOH. Furthermore, it appears that the effects of the different prewashes are substantially independent of each other, since in run 4 where the order of the two prewashes was reversed, the results are substantially the same. As a practical matter, it appears that removing 95% or more of the charge on the capillary wall is important in performing high resolution capillary electrophoresis, regardless of the prewash that is used. However, it appears that eliminating that charge is much easier to accomplish, and allows use of a much higher and more easily attained pH level, if the capillary is prewashed with an acid instead of a base before the run.

It will also be appreciated by those skilled in the art that there are several ways to control the temperature of the solvent/solute system. For example, one way has already been described which uses a heater system for environmental chamber 11. Another approach would be to use one or more electrical heaters wrapped around the capillary tube, and another would be to use one or more pieces of insulating wrap on the capillary tube. Those skilled in the art will undoubtedly be able to think of other equivalent methods for controlling the temperature to effect electrophoretic mobility. Those skilled in the art will also understand that in some instances it may be preferred to not have all components inside the enclosure 11. For example, the detector sometimes may be located outside the enclosure along with the corresponding portion of the capillary where the UV detection is to take place. Such an approach would facilitate service of th UV detector system. Also, instead of raising and lowering the capillary, one could raise and lower the sliding support to insert and remove the capillary from the sample and buffer reservoir. It should also be apparent that one could use electrophoretic media other than aqueous solutions, for example organic fluids could also be used, a specific example being acetonitrile.

APPENDIX A

SOFTWARE SPECIFICATION

CONFIDENTIAL Property of ABI/Santa Clara Analytical Division

|  |  |  |  |
|---|---|---|---|
|  | ii. | Equilibrate Temperature | 17 |
|  | iii. | Vacuum Wash Sequence | 17 |
|  | iv. | EquilibrateBuffer | 17 |
|  | v. | Marker Inject Sequence | 18 |
|  |  | v.b.1 Marker Vacuum Inject Sequence | 18 |
|  |  | v.b.2 Marker Voltage Inject Sequence | 18 |
|  | vi. | Sample Inject Sequence | 19 |
|  |  | vi.b.1 Vacuum Sample Inject Sequence | 19 |
|  |  | vi.b.2 Voltage Sample Inject Sequence | 19 |
|  | vii. | Detector Sequence | 19 |
|  | viii. | t Zero Sequence | 20 |
|  | ix. | t1 Sequence | 20 |
|  | ix. | t2 Sequence | 20 |
|  | x. | t3 Sequence | 20 |
|  | xi. | t End Sequence | 21 |
| F. | Specialized Sequences | | 22 |
| | 1. | Capillary Vial holder Sequence | 22 |
| | | 1.2 Rotate Sequence | 22 |
| | | 1.3 Up Vial Holder Sequence | 23 |
| | | 1.4 Down Vial Holder Sequence | 23 |
| | 2. | Power On Sequence | 23 |
| | 3. | Self Test Sequence | 23 |
| | 4. | Power Fail Sequence | 24 |
| | 5. | Real Time Clock Sequence | 24 |
| | 6. | Printer Sequence | 24 |
| | 7. | Buffer Bottle Status Sequence | 24 |
| | 8. | Adjust 5" Vacuum Sequence | 25 |
| | 9. | Power Down Sequence | 25 |
| | 10. | Interrupt Service Routine | 25 |
| | 11. | Round Robin Tasks | 26 |

III. Manual Control . . . . . . . . . . . . . . . . . . . . . . . 27

IV. Configuration . . . . . . . . . . . . . . . . . . . . . . . . 28

V. System Screens . . . . . . . . . . . . . . . . . . . . . . . 29
   A. Idle Screen . . . . . . . . . . . . . . . . . . . . . . . 29
   B. Edit with Run in process Screen . . . . . . . . . . . 29
   C. Manual Screen . . . . . . . . . . . . . . . . . . . . . 29

VI. Error Handling . . . . . . . . . . . . . . . . . . . . . . . 30
   A. Error Screens . . . . . . . . . . . . . . . . . . . . . 30

VII. Hardware/Software Interface . . . . . . . . . . . . . . . . 31
   A. Autosampler Controller . . . . . . . . . . . . . . . . 31
   B. Detector Controller . . . . . . . . . . . . . . . . . . 31
   C. Temperature Controller . . . . . . . . . . . . . . . . 32
   D. Vacuum Controller . . . . . . . . . . . . . . . . . . . 33
   E. Voltage Controller . . . . . . . . . . . . . . . . . . 34

CONFIDENTIAL Property of ABI/Santa Clara Analytical Division A-iii

CONFIDENTIAL Property of ABI/Santa Clara Analytical Division
Thursday February 11, 1988 4:09pm

Table of Contents:

I. Operational Description . . . . . . . . . . . . . . . . . . 1
   A. Functional Layout . . . . . . . . . . . . . . . . . . 1
   B. Mode Descriptions . . . . . . . . . . . . . . . . . . 2
      1. Idle Mode . . . . . . . . . . . . . . . . . . . 2
         a. Edit Method . . . . . . . . . . . . . . . 2
         b. Run Method . . . . . . . . . . . . . . . . 3
         c. Manual Control . . . . . . . . . . . . . . 3
         d. Configuration . . . . . . . . . . . . . . 3

II. Methods . . . . . . . . . . . . . . . . . . . . . . . . . 4
   A. Description of Parameters . . . . . . . . . . . . . . 4
      1. Wash Time . . . . . . . . . . . . . . . . . . . 4
      2. Buffer Equilibration Time . . . . . . . . . . . 5
      3. Marker Injection Time . . . . . . . . . . . . . 5
      4. Sample Injection Time . . . . . . . . . . . . . 5
      5. Polarity . . . . . . . . . . . . . . . . . . . . 5
      6. Wavelength . . . . . . . . . . . . . . . . . . . 6
      7. Range . . . . . . . . . . . . . . . . . . . . . 6
      8. Risetime . . . . . . . . . . . . . . . . . . . . 6
      9. Autozero . . . . . . . . . . . . . . . . . . . . 6
      10. Time . . . . . . . . . . . . . . . . . . . . . 6
      11. Buffer Number . . . . . . . . . . . . . . . . 7
      12. Voltage . . . . . . . . . . . . . . . . . . . 7
      13. Temperature . . . . . . . . . . . . . . . . . 7
   A.1 Fixed Parameters . . . . . . . . . . . . . . . . . . 8
      1. Temperature Equilibration Time . . . . . . . . 8
      2. Inject Vacuum Level . . . . . . . . . . . . . . 8
      3. Inject Voltage . . . . . . . . . . . . . . . . 8
   B. Method Execution . . . . . . . . . . . . . . . . . . 9
      1. Temperature Equilibration . . . . . . . . . . . 9
      2. Wash . . . . . . . . . . . . . . . . . . . . . . 9
      3. Buffer Equilibration . . . . . . . . . . . . . 10
      4. Marker Injection . . . . . . . . . . . . . . . 10
      5. Sample Number . . . . . . . . . . . . . . . . 10
      6. Sample Injection . . . . . . . . . . . . . . . 10
      7. Begin Final Run . . . . . . . . . . . . . . . 10
      7. End of Run . . . . . . . . . . . . . . . . . . 11
      8. Run Functions . . . . . . . . . . . . . . . . 11
      Pause Note . . . . . . . . . . . . . . . . . . 12
   C. Cycle Editing . . . . . . . . . . . . . . . . . . . 13
      1. Method Choices . . . . . . . . . . . . . . . . 13
        Sample Method Possibilites . . . . . . . . . 13
        State Diagram . . . . . . . . . . . . . . . . 14
   D. Method Memory . . . . . . . . . . . . . . . . . . . 15
   E. Cycle Sequences . . . . . . . . . . . . . . . . . . 16
      i. Interlocks . . . . . . . . . . . . . . . . . . 16
        i.a Interlock Sequence . . . . . . . . . . . 16

CONFIDENTIAL Property of ABI/Santa Clara Analytical Division A-ii

CONFIDENTIAL Property of ABI/Santa Clara Analytical Division
Thursday February 11, 1988

|      |                                       |    |
|------|---------------------------------------|----|
| F.   | Polarity Relay                        | 34 |
| G.   | Event Relay                           | 35 |
| H.   | Heater Flap Relay                     | 35 |
| VIII.| State Notes                           | 36 |
| 1.   | Interlocks                            | 36 |
| 2.   | Equalize Temperature                  | 36 |
| 3.   | Vacuum Wash                           | 36 |
| 4.   | Equalize Buffer                       | 36 |
| 5.   | Marker Inject General Operation       | 36 |
| 6.   | Sample Inject General Operation       | 36 |
| 7.   | Inject Vacuum                         | 36 |
| 8.   | Inject Voltage                        | 36 |
| 9.   | t Zero Event Processing               | 36 |
| 10.  | Integrator                            | 36 |
| 11.  | Start Automatic Operation             | 36 |
| 12.  | End Automatic Operation               | 36 |
| 13.  | Start/End Manual Operation            | 36 |
| 14.  | Rotate Vials                          | 37 |
| 15.  | Down Vials                            | 37 |
| 16.  | Up Vials                              | 37 |
| 17.  | ISR                                   | 37 |
| 18.  | Round Robin Operation                 | 37 |
|      | a. Software Interlock Mirror Check    | 37 |
|      | b. Voltage A/D                        | 37 |
|      | c. Vacuum A/D                         | 37 |
|      | d. Temperature A/D                    | 37 |
|      | e. Absorbance A/D                     | 37 |
|      | f. Status display update              | 37 |
|      | g. Chemistry                          | 37 |
|      | h. Run Setup                          | 37 |
|      | i. Edit                               | 37 |
|      | j. Print                              | 37 |
|      | k. RS-232                             | 37 |

CONFIDENTIAL Property of ABI/Santa Clara Analytical Division 4-iv

CONFIDENTIAL Property of ABI/Santa Clara Analytical Division
Thursday February 11, 1988 4:09pm I. Operational Description:

The software will have three primary operating modes. These are Idle, Run, and Manual. Each of these modes relates to a basic state of operation for the instrument. Each of the primary modes have a series of associated sub-modes.

A. Functional Layout:

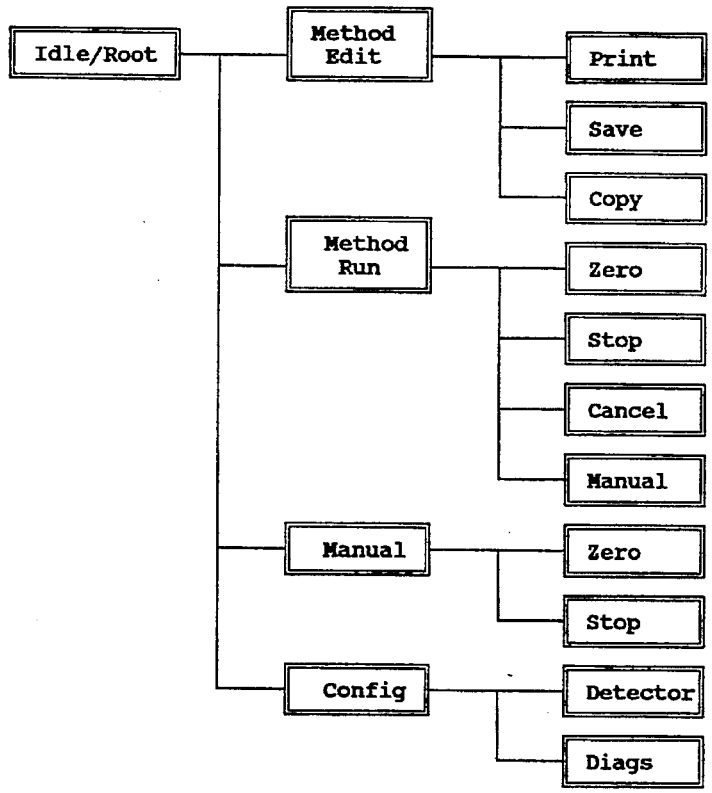

CONFIDENTIAL Property of ABI/Santa Clara Analytical Division   A-1

CONFIDENTIAL Property of ABI/Santa Clara Analytical Division
Thursday February 11, 1988 4:09pm

B. Mode Descriptions:

Each Mode is selected by using the special function keys to the right of the display. Choices are presented to the chemist on the display and by using the NEXT and PREVIOUS keys changes the appropriate values in the appropriate units for the particular choice being edited or selected. To change from choice to choice the Left and Right Arrow keys are used.

The following are brief descriptions of the instrument's modes.

1. Idle Mode:

This is the power on and default operating mode of the instrument. Any of the other modes may be started from idle, and return to idle when they are exited. Idle allows the user to execute the functions listed below.

a) Cycle Edit
    b) Method Run
    c) Manual Control
    d) Configuration

Doors may be opened in Idle mode at anytime.

a. Edit Method:

Allows the chemist to display, and modify saved methods or to copy a method into a new method name for editing. The system will maintain in [ battery backed up ] RAM between 1 and 20 methods. The system will contain in ROM example executable methods [ 1-20 ] which can be copied into RAM and be edited. This function will allow the chemist to access a method, modify it and save it back. All method parameters will be validated at input, and prior to saving. The list of method parameters, and their meaning will be presented later.

Editing of any RAM based method can occur during a method run but will not change the method run in process. Changes made to the method in process will be seen the next time that method is run.

CONFIDENTIAL Property of ABI/Santa Clara Analytical Division A-2

CONFIDENTIAL Property of ABI/Santa Clara Analytical Division
Thursday February 11, 1988 4:09pm b. Run Method:

Allows the chemist to execute one of the saved methods automatically. Execution performs the following set of cycles, in the order shown. Doors can be opened only when a pause state is in process. With the combination of RAM and ROM methods there will be a total of 40 methods available to the chemist.

| | | |
|---|---|---|
| i) | Interlocks | All interlocks are verified. |
| ii) | Wash | Capillary washed w/ reagent. |
| iii) | Equil Buffer | Buffer is brought into the capillary and equilibrated. |
| iv) | Marker Inj. | Marker solution injected. |
| v) | Sample Inj. | Sample solution injected. |
| vi) | Detector | Initialize Detector |
| vii) | t0 | Initial Time Step. |
| viii) | t1 | First Change Option. |
| ix) | t2 | Second Change Option. |
| x) | t3 | Third Change Option. |
| xi) | tEnd Run | Run continues until this time expires, or stop/abort pressed. | c. Manual Control:

In this mode the chemist can set instrument parameters from the key board with realtime results. Introduction of solutions from vials is allowed, but the sequence of solution introduction is carefully controlled when HIGH VOLTAGES are involved. High voltage is allowed only when capillary is in a sample or buffer position, and all safety interlocks are verified. Doors may be opened in the manual mode when no voltage is applied to the capillary and the vial holder is not moving.

d. Configuration:

This allows the chemist to set default values for the system parameters. This includes all detector parameters.
Self test is executed at power up doing only those tests that do not require user intervention, and whenever diagnostics are required all tests are available.
Adjustment of capillary is accomplished at this state allowing the vial holder to be in the up position with the doors open.

CONFIDENTIAL Property of ABI/Santa Clara Analytical Division A-3

CONFIDENTIAL Property of ABI/Santa Clara Analytical Division
Thursday February 11, 1988 4:09pm

II. Methods:

A. Description of Parameters:

The ACE will be capable of running up to four (4) samples unattended by the chemist. To do this the system must know in advance the values for a set of control parameters. This set of parameters will be called an ACE method.

The following is a list of the parameters in an ACE method.

1) Wash Time
2) Buff Equil Time
3) Marker Inj Time
4) Sample Inj Time
5) Polarity
6) Wavelength
7) Range
8) Risetime
9) Autozero
10) Time
11) Buffer Number
12) Voltage
13) Temperature Each of these parameters is used during an automated run to control the instrumental conditions. [ The last four parameters are optionally changeable three times during an ACE method run. ]

Some of the parameters are not currently set by the chemist, but use instead preset values determined by ABI/SC chemists.

1) Temperature Equil Time
2) Inject Vacuum Level
3) Inject Voltage

1. Wash Time:

Range:   0 - 60 min
Default: 5 min
Unit:    1 min

The wash time is how long a strong buffer is applied to the capillary as the first step in an automated run. If this time is set to zero, this step in the run sequence will not occur.

CONFIDENTIAL Property of ABI/Santa Clara Analytical Division 4-4

CONFIDENTIAL Property of ABI/Santa Clara Analytical Division
Thursday February 11, 1988 4:09pm

2. Buffer Equilibration Time:

Range:    0 - 20 min
    Default:  1 min
    Unit:     1 min

The third step of the run procedure is to introduce the buffer into the capillary. This is performed by a vacuum sucking on one end of the capillary. This time is variable, and can be set by the chemist. Temperature equilibration could take place at the same time possibly. If this time is set to zero, this step in the run sequence will not occur.

3. Marker Injection Time:

Range:    0 - 30 sec
    Default:  1 sec
    Unit:     25ms accuracy .5 second increments The marker solution is introduced into the capillary at the end of the equilibration state. A very small amount (a few $\mu L$) of this solution is introduced as a plug into the end of the capillary, by using a lower vacuum for a controlled period of time.

4. Sample Injection Time:

Range:    0 - 30 sec
    Default:  3 sec
    Unit:     25ms accuracy .5 second increments The sample solution is introduced next into the capillary as a second small plug. Again the volume injected is a function of vacuum level, time, viscosity and capillary dimensions.

5. Polarity:

Range:    A | C
    Default:  Anode [ at sampling side ]
    Unit:     N/A

The polarity of the sample side buffer vial can be either positive or negative. This value is set in the method and is maintained for the length of the run.

CONFIDENTIAL Property of ABI/Santa Clara Analytical Division    A-5

CONFIDENTIAL Property of ABI/Santa Clara Analytical Division
Thursday February 11, 1988 4:09pm

6. Wavelength:

Range:    190 - 700 nm
Default:  215 nm
Unit:     1 nm

The absorbance wavelength of the detector for the run. This value is user set at the start of the run, and remain constant through out the run.

7. Range:

Range:    0.001 - 3.000 AUFS
Default:  0.01 AUFS
Unit:     0.001 - 0.1 is 0.001; 0.1 - 3.000 is 0.01 AUFS The absorbance units full scale of the detector is user set at the start of the run and remains constant for the duration of the run.

8. Risetime:

Range:    0.02 - 5.0 secs
Default:  .5
Unit:     8 steps

The detector risetime (response time) is user set at the start of the run, and remains constant for the duration of the run. The value has 8 incremental values between 0.02 and 5.0 seconds.

9. Autozero:

Range:    Yes/No
Default:  Yes
Unit:     N/A

For the present system the detector will be autozeroed at a set time after the voltage is turned on in the run. [ See T Zero sequence ]

10. Time:

Range:    0.0 - 60.0 mins
Default:  25 mins
Unit:     1 min

The time along with the voltage, and temperature will be

CONFIDENTIAL Property of ABI/Santa Clara Analytical Division    A-6

CONFIDENTIAL Property of ABI/Santa Clara Analytical Division
Thursday February 11, 1988 4:09pm used to create a series of steps for the run to follow. This will be defined in the next section.

11. Buffer Number:

Range:    1 - 2
    Default:  1

There are two (2) buffer positions on the vial tray. Each method will need to know which buffer(s) is to be used with the run. [ Both buffers can be used in the same run. ] When buffer change is selected during a run the software will select the opposite buffer automatically the user will not need to specify a buffer number. When a buffer change is selected the voltage will be turned off during the change and will be turned on.

12. Voltage:

Range:    0 - 30 KV
    Default:  15 KV
    Unit:     1 KV

The value of the voltage is the potential across the ends of the capillary at the time specified. This value may range from 0 to 30 kilovolts.

13. Temperature:

Range:    15 - 60°C
    Default:  30°C
    Unit:     1°C

The value of the temperature is the temperature of the thermostated oven in the instrument at the time specified. It may range from 15 to 60°C. If the value entered is below 25°C than a caution will be displayed that coolant must be present to achieve desired temperature. In the future the software with a hardware ambient temperature detector will give this caution according to the temperature selected and the actual ambient temperature.

CONFIDENTIAL Property of ABI/Santa Clara Analytical Division   A-7

CONFIDENTIAL Property of ABI/Santa Clara Analytical Division
Thursday February 11, 1988 4:09pm

A.1 Fixed Parameters:

Some parameters are not currently set by the chemist, but use instead preset values determined by ABI/SC chemists.

1. Temperature Equilibration Time:

Future Range:　0 - 10 min
　　Fixed:　6 min

The primary step of an automated run is bringing the oven up to the runtime temperature. This value is set in the software, and cannot be changed by the chemist. If temperature is achieved prior to expiration of this time the run proceeds to the next step.

2. Inject Vacuum Level:

Range:　0 - 20 inches Hg
　　Default:　5 inches Hg
　　Future Unit:　1 inch

The vacuum level which is used to introduce the sample, and marker into the capillary is set in the software, and copied into the method when it is first created.

3. Inject Voltage:

Range:　0 - 30 KV
　　Default:　6 KV
　　Future Unit:　1KV

The voltage level at which sample and marker is electrophoresed into the capillary is set in the software.

CONFIDENTIAL Property of ABI/Santa Clara Analytical Division

CONFIDENTIAL Property of ABI/Santa Clara Analytical Division
Thursday February 11, 1988 4:09pm

B. Method Execution:

Section A above describes the instrumental parameters involved in an automated run performed on the ACE. This section will briefly describe cycle particular information and operation.

When the chemist selects the RUN method function, the software asks which method to run. A number between 1 and 20 is entered for the desired method. That method is then copied from the method buffers into the run buffer. At this time the chemist is asked the number of Samples to analyze using this method. The instrument then begins execution of the run buffer.

1. Temperature Equilibration:

An optional Pause can be performed before this step continues. [ See Pause Note ]
The second state in a run sequence is temperature equilibration. Oven is to start equilibration as soon as value is entered [ Manual Mode ] or as soon as a method number is selected [ Auto Mode ]. The oven temperature is set from the value in the time zero (0.0) step of the method. A period of up to six minutes is allowed for the oven to reach this temperature. The temperature is determined to have been reached when:

> 10 [ to be determined in actual use most likely a value of 2 ] sequentially acquired temperature values have delta between the set value, and the read value of $\pm$ .1°C precision; $\pm$ .2°C accuracy; read $\pm$ .25°C for 10 seconds .

When this condition is met, the run advances to the next state.

2. Wash:

An optional Pause can be performed before this step continues. [ See Pause Note ]
The first state in a run sequence is the WASH state. This state draws a strong acid or base solution through the capillary. This is done by positioning the capillary in the wash vial. The capillary is then exposed to a vacuum at the wash fixed level. This exposure has a time duration as set in the wash time.

CONFIDENTIAL Property of ABI/Santa Clara Analytical Division

CONFIDENTIAL Property of ABI/Santa Clara Analytical Division
Thursday February 11, 1988 4:09pm

3. Buffer Equilibration:

An optional Pause can be performed before this step continues. [ See Pause Note ]
The third state of a run is the equilibration of the buffer to the capillary. This is accomplished by moving the capillary to the buffer designated in the method. The buffer is then drawn through the capillary at the designate wash vacuum level, for the designated buffer equilibration time.

4. Marker Injection:

An optional Pause can be performed before this step continues. [ See Pause Note ]
The fourth state of a run is the injection of the marker solution into the capillary. This is accomplished by positioning the capillary into the marker vial. The marker is then drawn into the capillary for the designated injection time. The method of injection is by exposing the capillary to a vacuum at the injection level, or a voltage at the injection level.

5. Sample Number:

Range:   1 - 4
Default:  1

There will be four (4) sample positions on the vial holder. At the time a method run is selected the number of Samples to be analyzed will also be selected.

6. Sample Injection:

An optional Pause can be performed before this step continues. [ See Pause Note ]
The fifth state of a run is the injection of the sample into the capillary. The capillary is positioned to the designated sample vial, and the processed the same as a marker, except the exposure time is that of the sample inject time.

7. Begin Final Run:

An optional Pause can be performed before this step continues. [ See Pause Note ]
At this state actual electrophoresis begins. The polarity of the buffer is set per the method and the voltage is set to the level specified in the time zero (0.0) step of the method. A specified number of seconds after the voltage is turned on, the CONFIDENTIAL Property of ABI/Santa Clara Analytical Division A-10

CONFIDENTIAL Property of ABI/Santa Clara Analytical Division
Thursday February 11, 1988 4:09pm detector is sent the command to autozero itself, and the remote integrator event is executed.

Each method can have up to four (4) gradient steps associated with it. These steps are contain the information shown below:

Time:    Voltage:    Temperature:

The method steps are executed in time sequential order. Every method has a time 0.0 step. This sets the initial voltage and temperature for the run. If no other steps are entered, these conditions are maintained for the length of the run. If other steps are present the voltage and/or temperature are stepped over the time period between sequential method steps. The time of the final step is the total runtime of the method. For instance the following method would have a runtime of 30 minutes, and would have two state changes [ voltage & or temperature ].

| Time: | Voltage: | Temperature: |
|---|---|---|
| 0.0 min | 20 KV | 30 °C |
| 10.0 | 30 | 30 \| empty |
| 20.0 | 30 \| empty | 40 |
| 30.0 | 30 | 40 |

7. End of Run:

When the runtime has been reached, the voltage is turned off. At the same time the remote integrator event is executed again. The instrument then returns to the Idle mode. The temperature that was T zero temperature is maintained as the idle temperature before the next run.

8. Run Functions:

There are four functions available to the chemist during an automated run. The first of these is autozero. By executing this function, the chemist sends the detector the instruction to autozero itself. The second function when executed stops the methodmed run early. The third function aborts the methoded run at anytime in the sequence. The fourth function allows the chemist to go from automated control to manual control at the current conditions of the instrument.

CONFIDENTIAL Property of ABI/Santa Clara Analytical Division A-11

CONFIDENTIAL Property of ABI/Santa Clara Analytical Division
Thursday February 11, 1988 4:09pm

Pause Note:

SemiAutomatic operation will follow the same sequence as the automated operation with a pause at the beginning of the cycle. After the operator has been pushed the proceed button the automatic sequence will continue.

CONFIDENTIAL Property of ABI/Santa Clara Analytical Division A-12

CONFIDENTIAL Property of ABI/Santa Clara Analytical Division
Thursday February 11, 1988 4:09pm

C. Cycle Editing:

When a chemist executes the cycle edit function from the Idle mode, he is first quiered for the method number to edit. This method is then copied from the method buffers to the edit buffer. The editing screen/s are then presented to the chemist. The chemist can move between the edit fields to change the various method parameters. The cycle parameters are presented to the chemist and by using the NEXT and PREVIOUS keys changes the appropriate values in the appropriate units for the particular parameter being edited.

One function available during editing allows the chemist to save the changes back to the method buffer. When this function is executed, the entire method is validated, and then saved back to its method buffer. The editor is then exited, and the instrument is returned to the Idle condition.

A second function allows the chemist to print a method out. And a third function allows the chemist to modify the detector parameters.

1. Method Choices:

The following chart is a matrix showing the options and choices available when editing a run method.

Sample Method Possibilites

| Cycle | Time | Pause | Volt | Temp | Item | Other |
|---|---|---|---|---|---|---|
| Wash | X | X | N/A | N/A | N/A | N/A |
| Buffer | X | X | N/A | N/A | N/A | N/A |
| Marker | X | X | N/A | N/A | X | N/A |
| Sample | X | X | N/A | N/A | X | N/A |
| Detector | N/A | N/A | N/A | N/A | N/A | Rise, range, wave |
| T Zero | 0.0 | N/A | X | X | BUF | Polarity |
| T 1 | X | N/A | X | X | BUF | Optional |
| T 2 | X | N/A | X | X | BUF | Optional |
| T 3 | X | N/A | X | X | BUF | Optional |
| T End | X | N/A | | | | |

CONFIDENTIAL Property of ABI/Santa Clara Analytical Division A-13

CONFIDENTIAL Property of ABI/Santa Clara Analytical Division
Thursday February 11, 1988 4:09pm
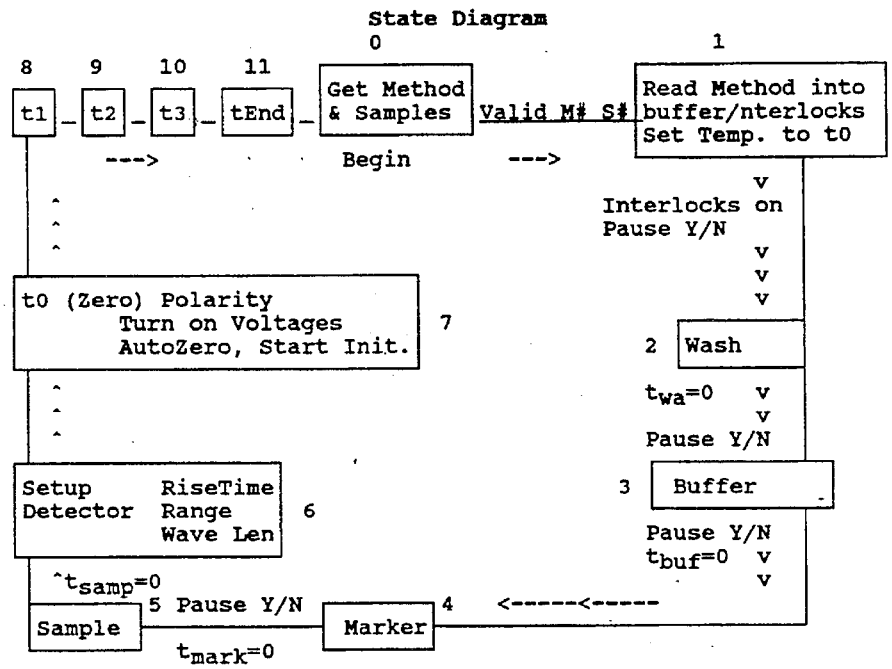
Key: t=time    T=Temperature
Notes:
    Boxes 2-5 time decreases to zero for completion of task.
    Boxes 7-11 time increase to chosen value for completion of task.
    Box 6 MUST occur within 6 minutes with the temperature stable.

CONFIDENTIAL Property of ABI/Santa Clara Analytical Division
Thursday February 11, 1988 4:09pm

D. Method Memory:

The ACE instrument will have the ability to save four (4) methods in battery backed memory. This will allow the chemist to establish a set of methods and then maintain those methods even when the instrument is turned off. In addition to the four methods, there will be two buffers to hold the method currently being edited, and the method currently executing. This means there will a total of six (6) method buffers in the battery backed ram. A method buffer should consume approximately 30 bytes of memory.

CONFIDENTIAL Property of ABI/Santa Clara Analytical Division
Thursday February 11, 1988 4:09pm

E. Cycle Sequences:

The following section contains the sequence of events that are to take place for each operation. This is the start of the State definitions that the software will implement to create the desired use for the ACE unit.

i. Interlocks:

The following hardware interlocks prevent voltage from being applied to the capillary, rotation of the vial holder or up movement of the vial holder.

a. Buffer Door b. Detector Door c. Vial Holder Door d. Oven Access Door e. Vial Holder in Place f. Vial Holder in Rotate allowed position When the Doors can be opened or must be closed is indicated in the next two lists.

| Doors May be Open | Doors Must be Closed |
|---|---|
| 1. Idle Mode | 1. Voltage applied to capillary |
| 2. Manual Mode | 2. Vial Holder Moving |
| 3. Pause | | i.a Interlock Sequence:

a. Look at Hardware Bit b. Look at Software Mirrors of processes allowed
        1. The software Mirrors are flags indicating the processes occurring at that time. They get changed at cycle transitions, cycle operation and exit from the cycle.

CONFIDENTIAL Property of ABI/Santa Clara Analytical Division A-16

CONFIDENTIAL Property of ABI/Santa Clara Analytical Division
Thursday February 11, 1988 4:09pm ii. Equilibrate Temperature:

a. Read Oven Temperature from A/D and store value b. Read Ambient Temperature and store value c. Compare Oven Temperature to setpoint 1. If Reading > setpoint
       a. Delta Temperature > +15°C and ambient < Oven then open flap & turn off heater. Otherwise just turn heater off.

d. If Reading < setpoint then close flap & turn on heater.

Note: Checking ambient temperature and giving cautions for temperatures close to or lower than ambient will be a future design choice. Also in the future a valve to control coolant flow will be under software control.

iii. Vacuum Wash Sequence:

a. Move Vial Holder to Wash solution b. Make sure 5" and Inject valves are closed c. Open 20" valve d. Open Inject valve e. Wait X time [ user selected time ]

f. Close Inject valve g. Close 20" valve iv. EquilibrateBuffer:

a. move vial holder to designated buffer number b. Vacuum buffer c. Wait X time [ user selected time ]

CONFIDENTIAL Property of ABI/Santa Clara Analytical Division  4-17

CONFIDENTIAL Property of ABI/Santa Clara Analytical Division
Thursday February 11, 1988 4:09pm v. Marker Inject Sequence:

a. move vial holder to marker solution b. perform user choice of vacuum or voltage c. Wait X time [ user selected time ]

v.b.1 Marker Vacuum Inject Sequence:

a. Make sure 20" and Inject valves are closed b. Check 5" vacuum level c. Open 5" valve d. Check 5" vacuum level e. Open Inject valve f. Wait X seconds [ 0 - 30 seconds user selectable ]

g. Close Inject valve i. Close 5" valve j. Adjust 5" vacuum level v.b.2 Marker Voltage Inject Sequence:

a. Check Marker position b. Check Interlocks & in Up position c. Write to D/A voltage desired [ Fixed value at this time]

d. Read A/D for current to indicate voltage conducting

CONFIDENTIAL Property of ABI/Santa Clara Analytical Division A-18

CONFIDENTIAL Property of ABI/Santa Clara Analytical Division
Thursday February 11, 1988 4:09pm vi. Sample Inject Sequence:
- a. move vial holder to sample number desired
- b. perform user choice of vacuum or voltage
- c. Wait X time [ user selected time ]

vi.b.1 Vacuum Sample Inject Sequence:
- a. Make sure 20" and Inject valves are closed
- b. Check 5" vacuum level
- c. Open 5" valve
- d. Check 5" vacuum level
- e. Open Inject valve
- f. Wait X seconds [ 0 - 10 seconds user selectable ]
- g. Close Inject valve
- i. Close 5" valve
- j. Adjust 5" vacuum level vi.b.2 Voltage Sample Inject Sequence:
- a. Check Marker position
- b. Check Interlocks & in Up position
- c. Write to D/A voltage desired [ Fixed value at this time]
- d. Read A/D for current to indicate voltage conducting vii. Detector Sequence:
- a. Set Wave Length
- b. Set Range
- c. Set Rise Time CONFIDENTIAL Property of ABI/Santa Clara Analytical Division  A-19

CONFIDENTIAL Property of ABI/Santa Clara Analytical Division
Thursday February 11, 1988 4:09pm viii.  t Zero Sequence:

a. Interlocks OK b. At Temperature c. Turn on Integrator d. Turn on voltage [ Stepped ONLY ] and start run time e. Send Autozero command to Detector ix.  t1 Sequence:

a. Go to next cycle if time is zero b. change voltage if non zero c. change temperature if non zero d. change buffer if non zero ix.  t2 Sequence:

a. Go to next cycle if time is zero b. change voltage if non zero c. change temperature if non zero d. change buffer if non zero x.  t3 Sequence:

a. Go to next cycle if time is zero b. change voltage if non zero c. change temperature if non zero d. change buffer if non zero CONFIDENTIAL Property of ABI/Santa Clara Analytical Division  A-20

CONFIDENTIAL Property of ABI/Santa Clara Analytical Division
Thursday February 11, 1988 4:09pm xi. t End Sequence:

a. Turn off Voltage b. Set temperature to what it was at time Zero c. turn off integrator d. Decrement number of samples to run i. if number of sample = zero than go to Idle
        ii. if number of samples not = zero begin autorun on next cycle. The autorun restarts at the beginning of the method with temperature equalibration.

CONFIDENTIAL Property of ABI/Santa Clara Analytical Division A-21

CONFIDENTIAL Property of ABI/Santa Clara Analytical Division
Thursday February 11, 1988 4:09pm

P. Specialized Sequences:

The sequences in this section are ones that are used by larger general sequences. Specialized sequences that can not find a home elsewhere are included here.

1. Capillary Vial holder Sequence:

The time from vial to vial is 1/4 of a second giving a worse case of 1 3/4 seconds to the next vial. The following chart shows the positions and coding for each of the eight possible vials.

Direction of rotation is ------------->

| VIALS | Sam1 | Sam2 | Sam3 | Sam4 | Wash | Buf2 | Buf1 | Marker |
|---|---|---|---|---|---|---|---|---|
| Rough LED 1 |  | x |  |  | x |  | x | x |
| Rough LED 2 |  |  | x |  | x | x |  | x |
| Rough LED 3 |  |  |  | x |  | x | x | x |
| Exact LED | x | x | x | x | x | x | x | x |

1.2 Rotate Sequence:

a. Sampler Down and at IN position b. Turn Motor On c. Watch for Rough LED Pattern d. When Exact LED is ON turn Motor OFF e. Move Sampler Up CONFIDENTIAL Property of ABI/Santa Clara Analytical Division  A-22

CONFIDENTIAL Property of ABI/Santa Clara Analytical Division
Thursday February 11, 1988 4:09pm

1.3 Up Vial Holder Sequence:

a. check interlocks b. make sure IN position, not rotating & volts off c. move up d. stop when up

1.4 Down Vial Holder Sequence:

a. Volts off, Vacuum off & interlocks OK b. Move Down c. Stop when indicator shows it is down

2. Power On Sequence:

a. Initialize peripheral components b. Initialize ports c. Initialize vacuum d. Idle position vial holder e. Set Temperature to 30° C f. display Idle mode screen

3. Self Test Sequence:

a. Choice run A test or Auto run tests b. Run test(s)

c. Report result(s)

d. Wait here for operator to go back to Idle menu

CONFIDENTIAL Property of ABI/Santa Clara Analytical Division A-23

CONFIDENTIAL Property of ABI/Santa Clara Analytical Division
Thursday February 11, 1988 4:09pm

4. Power Fail Sequence:

a. Save time occured b. Save system status if needed c. Turn off voltage, vacuum, motor movement d. Wait for power to be restored e. query operator for choices of recovery

5. Real Time Clock Sequence:

a. get command to be passed to chip b. send command c. get response if needed

6. Printer Sequence:

a. Get pointer of data to be printed b. Initialize printer c. Get format for this data to be printed d. Start print data in proper format e. Complete printer operation

7. Buffer Bottle Status Sequence:

a. Increment Buffer 1 & 2 number of times used counters b. If near depletion than give gentle caution c. If at or past depletion give firm warning d. reinitialize values as appropriate.

CONFIDENTIAL Property of ABI/Santa Clara Analytical Division
Thursday February 11, 1988 4:09pm 8. Adjust 5" Vacuum Sequence:

a. Read Vacuum A/D b. Compare to setpoint c. if reading > setpoint - XX    then open bleed down valve.

d. if reading < setpoint + XX    then open bleed up valve.

9. Power Down Sequence:

a. query operator for Choices b. save status according to operator choices c. put vial holder in store position.

d. Give operator OK to power down.

10. Interrupt Service Routine:

a. Check Hardware Interlock bit b. Increment Timer Counters c. Future read ports to see they are at state desired CONFIDENTIAL Property of ABI/Santa Clara Analytical Division A-25

CONFIDENTIAL Property of ABI/Santa Clara Analytical Division
Thursday February 11, 1988 4:09pm

11. Round Robin Tasks:

a. Software Interlock Mirror Check ( Future when can read ports)

b. Voltage task

1. Read A/D and convert to system value
        2. Adjust Voltage as needed
        3.

c. Vacuum task d. Temperature task e. Absorbance task f. Status display update g. Chemistry h. Run Setup i. Edit j. Print k. RS-232 l. Manual Operation

CONFIDENTIAL Property of ABI/Santa Clara Analytical Division A-26

CONFIDENTIAL Property of ABI/Santa Clara Analytical Division
Thursday February 11, 1988 4:09pm

III. Manual Control:

Manual control allows the chemist to perform any of the cycles of an automated run, but with complete manual control of the process. This will allow the chemist to test new ideas, and conditions in a manner where instant feed back to the changes are desired.

Manual Control will also have access to sub-state operations that are normally buried within an automated cycle. An example of such sub-cycles are the vial holder movement operations.

Manual control can be entered from two distinct places. The first place is the Idle mode. There will be a function key defined as manual control. The second place is from the Run mode. Again there will be a function key (preferable the same key) designated as Manual control.

When manual control is entered from the Idle mode, the instrument sets itself to the wash state of an automated run, but does not begin execution of the cycle. It waits for the chemist to specify which cycle it should execute, and what the conditions are.

When manual control is entered from the Run mode, the instrument continues running the current cycle. If the tEnd cycle has been entered, the voltage, and temperature are frozen, and the instrument continues to operate at those conditions, until either the conditions are changed or stopped by the chemist. The chemist may choose to abort or allow the current cycle to complete.

When in manual mode, the chemist may select a cycle to execute. The chemist than enters values for that cycle's parameters. If all conditions for that cycle are met than it is executed. This includes, safety interlocks, positioning of capillary, and any other safety related items.

CONFIDENTIAL Property of ABI/Santa Clara Analytical Division
Thursday February 11, 1988 4:09pm

IV. Configuration:

Configuration allows the chemist to do two things. They can set the default values of instrument parameters and self test the instrument.

Default instrument parameters such as the detector parameters that do not change as often as other instrument values can be set here, and any time a default value for that parameter is required, the software gets from the system configuration.

The instrument self test allows the operator to force the instrument to perform its power up diagnostics. These will be defined as they are deemed necessary.

CONFIDENTIAL Property of ABI/Santa Clara Analytical Division A-28

CONFIDENTIAL Property of ABI/Santa Clara Analytical Division
Thursday February 11, 1988 4:09pm

V. System Screens:

A. Idle Screen:

```
Line 1        Time TOD   Abs       Temp            Edit
Line 2        Volts      Current   Y               Run
Line 3
Line 4
Forty gage    12345678901234567890123456789012345 67890
                       1         2         3         4
```

B. Edit with Run in process Screen:

```
Line 1        Method  "Name"  Cycle "Name"         Main-
Line 2        Temp XX  Volts XX                    Run--
Line 3-       Time XX  Buffer X                    Print
Line 4        Temp: XX Volts XX End XX Time XX             Status
Forty gage    12345678901234567890123456789012345 67890
                       1         2         3         4
```

C. Manual Screen:

```
Line 1
Line 2
Line 3
Line 4
Forty gage    12345678901234567890123456789012345 67890
                       1         2         3         4
```

CONFIDENTIAL Property of ABI/Santa Clara Analytical Division  A-29

CONFIDENTIAL Property of ABI/Santa Clara Analytical Division
Thursday February 11, 1988 4:09pm

VI. Error Handling:

There will be visual and audible error response to all errors. Each cycle that has error checking will have a section for error processing which will include message display and corrective action if possible and if not an appropriate shutdown procedure.

A. Error Screens:

```
Line 1        Interlocks Faulty Check Doors & Sampler
Line 2
Line 3
Line 4
Forty gage    12345678901234567890123456789012345678 90
                       1         2         3         4
```

CONFIDENTIAL Property of ABI/Santa Clara Analytical Division A-30

CONFIDENTIAL Property of ABI/Santa Clara Analytical Division
Thursday February 11, 1988 4:09pm

VII. Hardware/Software Interface:

The information in this section will specify the relevant aspects of the hardware that the software needs for interface to the hardware. This includes port addresses of devices, control values of devices, and conversions for DACs, and ADCs.

A. Autosampler Controller:

Port:    73h

Autosampler consists of a pair of DC motors that are used to position a device. These motors are turned on and off, and the position is noted by monitoring a set of sensors. The bit pattern of the sensors indicates the position of the autosampler.

B. Detector Controller:

Port:    72h

At this stage the Detector Controller consists of an ADC to convert the absorbance signal from the back of the 783 detector to a digital value, and then display it. Other control of the detector will be via the Z80's RS-232c port.

CONFIDENTIAL Property of ABI/Santa Clara Analytical Division A-31

CONFIDENTIAL Property of ABI/Santa Clara Analytical Division
Thursday February 11, 1988 4:09pm

C. Temperature Controller:

Port:    71h

The temperature is controlled by reading the temperature value, comparing it to the setpoint value, and then turning the heater on/off and the opening/closing the flap to adjust the temperature up or down.

The following is the derivation of the temperature ADC reading to a temperature in °C.

$0$ to $5$ $V_{in}$ = $0$ to $60$ °C
  $255$ bits = $60$ °C
    $1$ bit = $0.253$ °C (ADC value * 253) / 1000 = T °C $0$ to $5$ $V_{in}$ = $10°$ to $60$ °C
  $255$ bits = $50$ °C
    $1$ bit = $0.196$ °C (ADC value * 196) / 1000 = T °C $0$ to $5$ $V_{in}$ = $15°$ to $60$ °C  per parameter temperature spec.
  $255$ bits = $45$ °C
    $1$ bit = $0.1765$ °C (ADC value * 176.5) / 1000 = T °C The following is a list of valid values that can be written out to port 71h for controlling the heater.

| | |
|---|---|
| 00h | Turn heater off. |
| 01h | Turn heater on. |

CONFIDENTIAL Property of ABI/Santa Clara Analytical Division  A-32

CONFIDENTIAL Property of ABI/Santa Clara Analytical Division
Thursday February 11, 1988 4:09pm

D. Vacuum Controller:

Port:    74h   Injector Valves
               75h   5 inch Ballast Level

The vacuum level in the ballast tanks is read through port 75h. The level of the ballast is maintained by reading the vacuum level, and then bleeding the tank up or down to adjust it. The bleed valves are controlled by writing a bit pattern to port 74h. Each bit position in the byte represents one of the valves.

The following derivation converts the A/D reading of the ballast level to vacuum in psi.

0 to 5 $V_{in}$ = 0 to 15 inches
      255 bits = 15 inches
        1 bit = .1197 inches of mercury (ADC value * 119.7) / 1000 = inches The following is a list of valid values that can be written out to the valve port (74h).

FBh      Turn On bleed-up valve.
    F7h      Turn On Bleed-down valve.
    EEh      Hi-Vacuum injector.
    EDh      Lo-Vacuum injector.

CONFIDENTIAL Property of ABI/Santa Clara Analytical Division A.33

CONFIDENTIAL Property of ABI/Santa Clara Analytical Division
Thursday February 11, 1988 4:09pm

E. Voltage Controller:

Port:  70h  High Voltage Control
       77h  High Voltage Current

The high voltage power supply uses a 0 to 10 V input to produce a 0 to 30,000 V output. The DAC value for the output voltage is written to port 70h. The current across the capillary is read at port 77h.

The following is derives the equation to convert a voltage setpoint into an DAC value:

$$0 \text{ to } 10 \ V_{in} = 0 \text{ to } 30{,}000 \ V_{out}$$
$$1 \ V_{in} = 3000 \ V_{out}$$
$$255 \text{ bits} = 10 \ V_{in}$$
$$1 \text{ bit} = 0.0392156 \ V_{in}$$

$$\frac{1 \ V_{in}}{3000 \ V_{out}} = \frac{0.0392156 \ V_{in}}{X \ V_{out}}$$

$$X \ V_{out} = 117.65 \ V_{out}$$

117.65 $V_{out}$ per 1 bit setpoint / 117.65 $V_{out}$ = DAC value
NOTE: setpoint is in increments of 1000 V This derivation converts the high voltage ADC reading to a value in Volts.

$$0 \text{ to } 4.95 \ V_{in} = 0 \text{ to } 0.33 \text{ mA}$$
$$255 \text{ bits} = 4.95 \ V_{in}$$
$$1 \text{ bit} = 0.0194117 \ V_{in}$$

The next derivation converts the current ADC reading to a current in $\mu A$.

F. Polarity Relay:

Port:  74h value of 20h

Engaged relay (on) gives a minus charge to the receive buffer side of the cathode. Disengaged relay (off) gives a plus charge to the receive buffer side of the cathode.

CONFIDENTIAL Property of ABI/Santa Clara Analytical Division  A-34

CONFIDENTIAL Property of ABI/Santa Clara Analytical Division
Thursday February 11, 1988 4:09pm

G. Event Relay:

Port:    74h value of 80h

This is the port used to turn on the Integrator.

H. Heater Flap Relay:

Port:    74h value of 40h

This port is used to let heat out of the box if it goes 15°C over the desired temperature.

CONFIDENTIAL Property of ABI/Santa Clara Analytical Division A-35

CONFIDENTIAL Property of ABI/Santa Clara Analytical Division
Thursday February 11, 1988 4:09pm

VIII. State Notes

1. Interlocks:

2. Equalize Temperature:

3. Vacuum Wash:

4. Equalize Buffer:

5. Marker Inject General Operation:

6. Sample Inject General Operation:

7. Inject Vacuum:

8. Inject Voltage:

```
    Use */Mod (n1,n2,n3 - ∆,n4) -> n1*n2/n3
Round up or down using remainder
: setpt -> Code ( <setpt - code> )
 Now rounded d/a setpiont code is on top of stack
:S      fetch
setpt -> code dup code! port p! ; Send it to D/A
```

A/D value (00-FF) * 13 (constant) = move decimal one place to left and get current reading in micro amps. [ 0-330 $\mu A$ ]

9. t Zero Event Processing:

10. Integrator:

11. Start Automatic Operation:

12. End Automatic Operation:

13. Start/End Manual Operation:

CONFIDENTIAL Property of ABI/Santa Clara Analytical Division A-36

CONFIDENTIAL Property of ABI/Santa Clara Analytical Division
            Thursday February 11, 1988 4:09pm

14. Rotate Vials:

Enter: Value of vial desired

```
       a.  At down yes/no
            no 1.  Alarm error exit
yes    b.  Get value of vial position
       c.  Turn on Motor
       d.  Read rough LED's wait for match yes/no
            no 1.  loop here till match
                  a.  get time & save first entry
                  b.  see if time > than 2 sec. yes/no
                  no loop & look for match
                  yes Alarm error exit
yes    e.  Read Exact LED wait for match yes/no
            no 1.  loop here till match
                  a.  get time & save first entry
                  b.  see if time > than 1/8 sec. yes/no
                  no loop & look for match
                  yes Alarm error exit
yes    f.  Turn Motor off
       g.  Clear stack of time data
       h.  Continue next sequence
```

Exit: At vial location desired

Error Exit:
```
              a.  buzzer on
              b.  display error message [ See display routine ]
              c.  go to Idle mode [ See Abort Sequence ]
```

15. Down Vials:

16. Up Vials:

17. ISR:

18. Round Robin Operation:
a. Software Interlock Mirror Check ( Future when can read ports)
b. Voltage A/D
c. Vacuum A/D
d. Temperature A/D
e. Absorbance A/D
f. Status display update
g. Chemistry
h. Run Setup
i. Edit
j. Print
k. RS-232

CONFIDENTIAL Property of ABI/Santa Clara Analytical Division A-37

What is claimed is:

1. An apparatus for capillary electrophoresis comprising:

a first reservoir for holding a first electrophoretic solution, the first reservoir having a first pressure;

a second reservoir that is electrically isolated from said first reservoir for holding a second electrophoretic solution;

a sample reservoir located in proximity to said first reservoir for holding a sample to be electrophoresed, the sample reservoir having said first pressure;

a high voltage power supply connected between said first reservoir and said second reservoir;

a pressure reservoir having a second pressure that is lower than said first pressure;

a capillary tube in which to electrophorese said sample, said capillary tube having an inlet end and an outlet end, the inlet end being located in the first reservoir during electrophoresis and in the sample reservoir during sample introduction;

connecting means for connecting said second reservoir to said pressure reservoir, said connecting means comprising valve means for venting said connecting means and for blocking communication between said second reservoir and said pressure reservoir while venting said connecting means;

inserting means for inserting the inlet end of said capillary tube into said sample reservoir and into said first reservoir, and computer means for controlling said insertion means and said valve means, so that when said inlet end of said capillary tube is in said sample reservoir, said valve means permits communication of said second reservoir with said pressure reservoir for a period of time for sucking said sample from said sample reservoir into said capillary tube.

2. An apparatus as in claim 1 wherein said computer means causes said inlet end of said capillary tube to be transferred to said first reservoir after said sucking of said sample into said capillary tube.

3. An apparatus as in claim 1 wherein said computer means includes means for controlling said high voltage power supply to cause electrophoresis in said capillary tube after said inlet end of said capillary tube is transferred into said first reservoir.

* * * * *